United States Patent [19]

Sprecker et al.

[11] 4,103,036

[45] Jul. 25, 1978

[54] FLAVORING WITH DERIVATIVES OF 1-ACETYL-3,3-DIMETHYLCYCLOHEXANE, AND PROCESSES FOR USING SAME AND PROCESSES FOR PREPARING SAID 1-ACETYL-3,3-DIMETHYLCYCLOHEXANE DERIVATIVES

[75] Inventors: Mark A. Sprecker, Sea Bright; Manfred Hugo Vock, Locust; Frederick Louis Schmitt, Holmdel; John B. Hall, Rumson; James Milton Sanders, Eatontown, all of N.J.

[73] Assignee: International Flavors & Fragrances Inc., New York, N.Y.

[21] Appl. No.: 819,955

[22] Filed: Jul. 28, 1977

Related U.S. Application Data

[62] Division of Ser. No. 713,357, Aug. 11, 1976, Pat. No. 4,062,894.

[51] Int. Cl.$^2$ ............... A23L 1/226; A23L 1/235
[52] U.S. Cl. ............................................. 426/538
[58] Field of Search ....................................... 426/538

[56] References Cited

U.S. PATENT DOCUMENTS

| 3,928,456 | 12/1975 | Kovats et al. ........... 426/538 X |
| 3,956,392 | 5/1976 | de Haan ..................... 426/538 X |
| 4,021,488 | 5/1977 | Hall et al. ................. 426/538 X |

FOREIGN PATENT DOCUMENTS 1,435,887  5/1976  United Kingdom ............ 260/586 R

*Primary Examiner*—Joseph M. Golian
*Attorney, Agent, or Firm*—Arthur L. Liberman; Harold Haidt; Franklin D. Wolffe

[57] ABSTRACT

Processes and compositions are described for the use in foodstuff, chewing gum, toothpaste and medicinal product flavor and aroma, tobacco flavor and aroma, perfume and perfumed article aroma augmenting, enhancing and imparting compositions and as foodstuff, chewing gum, toothpaste, medicinal product, tobacco, perfume and perfumed article aroma imparting materials of one or more derivatives of 1-acetyl-3,3-dimethylcyclohexane having the generic formula:

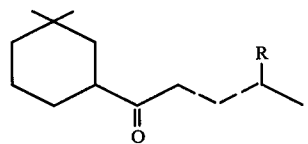

wherein one of the dashed lines may be a carbon-carbon single bond or a carbon-carbon double bond and the other of the dashed lines is a carbon-carbon single bond and R is hydrogen or methyl.

2 Claims, 7 Drawing Figures

FIG. 1
EXAMPLE II

NMR SPECTRUM

FIG. 2
EXAMPLE II

IR SPECTRUM

FIG. 3
EXAMPLE III
GC-MS PROFILE

FIG.4 EXAMPLE III

NMR SPECTRUM

IR SPECTRUM

FIG.5
EXAMPLE III

FIG. 6
EXAMPLE IV

NMR SPECTRUM

SOLVENT: $CDCl_3$
SWEEP WIDTH: 1000 Hz.

IR SPECTRUM

FIG. 7
EXAMPLE IV

FLAVORING WITH DERIVATIVES OF 1-ACETYL-3,3-DIMETHYLCYCLOHEXANE, AND PROCESSES FOR USING SAME AND PROCESSES FOR PREPARING SAID 1-ACETYL-3,3-DIMETHYLCYCLOHEXANE DERIVATIVES

This application is a divisional of application for U.S. patent Ser. No. 713,357 filed on Aug. 11, 1976, now U.S. Pat. No. 4,062,894 issued on Dec. 13, 1977.

BACKGROUND OF THE INVENTION

The present invention relates to derivatives of 1-acetyl-3,3-dimethylcyclohexane having the generic structure:

wherein one of the dashed lines is a carbon-carbon single bond or a carbon-carbon double bond and the other of the dashed lines is a carbon-carbon single bond and R is hydrogen or methyl, produced by the novel process of our invention and novel compositions using one or more of such 1-acetyl-3,3-dimethylcyclohexane derivatives to augment or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply and to provide more uniform properties in the finished product.

Sweet, fruity, raspberry, woody, lemon, piney, ionone-like, blueberry and floral aroma characteristics and sweet, raspberry, lemony, sweet fruity, red berry, piney, floral, ionone-like and nut meat flavor characteristics are particularly desirable for many uses in foodstuff flavorings, chewing gum flavors, toothpaste flavors and medicinal product flavors.

Fruity, woody, piney aromas with armoise and floral nuances and slight chocolate undertones are desirable in several types of perfume compositions, performed articles and colognes.

Acetylcyclohexane and 1-acetyl-3,3-dimethylcyclohexane are known substituents in perfumery. Thus, Arctander, "Perfume and Flavor Chemicals (Aroma Chemicals)," published in 1969, discloses acetylcyclohexane in Volume I, number 36:

"Peculiar camphoraceous-sweet odor with a certain amount of floral tones.

Although this chemical would primarily lend itself to perfume compositions in the Pine, Wood, Herbaceous and other non-floral types, it has a similarity to the harsh-floral types such as Hyacinth, etc. and its sweetness is sometimes classified as "musky"."

1-Acetyl-3,3-dimethylcyclohexane is disclosed as a fragrance material in U.S. Pat. No. 3,487,102, issued on Dec. 30, 1969.

The fragrance properties of the aforementioned acetyldimethylcyclohexane derivatives are different in kind from the fragrance properties of the compounds of the instant invention.

Firmenich's Dutch published application No. 7500838 discloses the preparation of the compound having the structure:

and discloses its use in perfumery and in augmenting foodstuff flavors. The perfumery use of this compound and other members of its class as "floral, green, herbaceous and chypre" useful in galbanum resinoids is also disclosed.

The compounds disclosed in Dutch published application No. 7500838 have organoleptic properties which causes them to be different in kind from the 1-acetyl-3,3-dimethylcyclohexane derivatives of our invention, which have unobvious, unexpected and advantageous characteristics in the field of augmenting or enhancing the organoleptic impressions of foodstuffs, foodstuff flavors, perfumes, perfumed articles and medicinal products.

THE INVENTION

It has now been discovered that novel solid and liquid foodstuff, chewing gum, medicinal product and toothpaste compositions and flavoring compositions therefor having sweet, fruity, raspberry, woody, lemon, piney, ionone-like, blueberry and floral aroma characteristics and sweet, raspberry, lemony, sweet fruity, red berry, piney, floral, ionone-like and nut meat flavor characteristics and novel perfume compositions, colognes and perfumed articles having fruity, woody, piney aromas with armoise and floral nuances and slight chocolate undertones, may be provided by the utilization of one or more 1-acetyl-3,3-dimethylcyclohexane derivatives having the formula:

wherein one of the dashed lines is a carbon-carbon single bond or a carbon-carbon double bond and the other of the dashed lines is a carbon-carbon single bond and R is hydrogen or methyl, in foodstuffs, chewing gums, toothpastes and medicinal product flavors.

The 1-acetyl-3,3-dimethylcyclohexane derivatives useful as indicated supra may be produced preferably by a process which comprises reaction of 1-acetyl-3,3-dimethylcyclohexane with an aldehyde having the structure:

thereby producing a compound having the structure:

wherein one of the dotted lines is a carbon-carbon double bond and the other of the dotted lines is a carbon-carbon single bond; in the presence of an inorganic base or a mixture of boron oxide ($B_2O_3$) and boric acid and utilizing the resulting product for its organoleptic properties or reducing the resulting product with hydrogen thereby producing a compound having the structure:

wherein R is hydrogen or methyl.

The first reaction with aldehyde having the structure:

is carried out at a temperature of from about 20° up to 160° C, when using a catalyst which is an inorganic base, such as an alkali metal hydroxide, for example, potassium hydroxide, sodium hydroxide and lithium hydroxide or an alkaline earth metal hydroxide such as barium hydroxide or lithium hydroxide; or at a temperature in the range of from about 100° up to 200° C when using a catalyst which is a mixture of boric acid ($HBO_3$) and boron oxide.

The time of reaction is inversely proportional to the temperature of reaction. Thus, when using a mixture of boric acid and boron oxide the time of reaction varies between 2 and 10 hours and when using a higher temperature the time of reaction varies from between 1 and 8 hours.

When using an inorganic base, the mole ratio of inorganic base:1-acetyl-3,3-dimethylcyclohexane may vary from 0.1:1 up to 2:1 with a mole ratio of 1:1 being preferred. When using the mixture of boric acid and boron oxide the mole ratio of boron oxide:1-acetyl-3,3-dimethylcyclohexane varies from 0.5:1 up to 1.5:1 with a mole ratio of 1:1 being preferred. The concentration of boric acid in the reaction mass may vary from 1 up to 80 grams per mole of aldehyde having the structure:

In all cases, the mole ratio of aldehyde having the structure:

:1-acetyl-3,3-dimethyl-cyclohexane may vary from 1:1 up to about 3:1 with a mole ratio of 2:1 being preferred.

Both reactions take place preferably in the presence of an inert solvent.

The reduction reaction to form the genus having the structure:

is carried out preferably in the presence of inert solvents such as isopropyl alcohol; at hydrogenation pressures of between 50 and 150 psig; at temperatures of between 25 and 150° C; and using hydrogenation catalysts such as 5% palladium-on-carbon, rhodium, platinum and Raney nickel. The time of reaction varies inversely with the temperature and pressure of reaction. Thus, lower pressures and temperatures give rise to a need for greater times of reaction. Thus, the time of reaction may vary from 1 hour up to 5 hours.

The previous reaction sequence is illustrated as follows:

Examples and organoleptic properties of materials produced according to the aforementioned process are as follows:

TABLE I

| NAME | STRUCTURE | ORGANOLEPTIC PROPERTIES | |
|------|-----------|---------|-----------|
| | | FLAVOR | FRAGRANCE |
| Mixture of 1-(3,3-dimethyl-cyclohexyl)-4-methyl-cis-2-penten-1-one, 1-(3,3-dimethyl-cyclohexyl)-4-methyl-trans-2-penten-1-one, and 1-(3,3-dimethylcyclohexyl)-4-methyl-3-penten-1-one | | Sweet, woody, raspberry, lemon, piney aroma character with sweet, raspberry and lemon flavor character at 1.0 ppm. | Fruity woody, piney aroma with armoise, floral nuances and a slight chocolate undertone. |
| Mixture of 1-(3,3-dimethyl-cyclohexyl)-cis-2-penten-1-one, 1-(3,3-dimethylcyclo-hexyl)-trans-2-penten-1-one, and 1-(3,3-dimethylcyclohexyl)-3-penten-1-one | | Sweet, raspberry, fruity, piney, floral, ionone-like aroma with sweet, sweet fruity, raspberry, red berry, piney, floral and ionone-like flavor characteristics. | Sweet, fruity, woody (pine) with pine-apple-galbanum, hexalon notes. |
| 3,3-dimethyl-1-(4-methylvaleryl)-cyclohexane | | Sweet, piney, fruity, blueberry, woody aroma character with sweet, piney, fruity, nut meat characteristics. | Low-keyed, sweet, woody, somewhat chocolate like. |

When the 1-acetyl-3,3-dimethylcyclohexane derivatives of our invention are used as food flavor adjuvants, the nature of the co-ingredients included with each of the said 1-acetyl-3,3-dimethylcyclohexane derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste."

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the 1-acetyl-3,3-dimethylcyclohexane derivative(s) of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta, beta-dimethylacrolein, methyl-n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethylnaphthalene, dodecane, methyldiphenyl, methylnaphthalene, myrcene, naphthalene, octadecane, tetradecane, tetramethylnaphthalene, tridecane, trimethylnaphthalene, undecane, caryophyllene, 1-phellandrene, p-cymene, 1-alpha-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, and acetals (e.g., 1,1-diethoxy-ethane, 1,1-dimethoxy-ethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the 1-acetyl-3,3-dimethylcyclohexane derivative(s) of our invention by not covering or spoiling the organoleptic properties (aroma and/or taste) thereof; (ii) be non-reactive with the 1-acetyl-3,3-dimethylcyclohexane derivative(s) of our invention and (iii) be capable of providing an environment in which the 1-acetyl-3,3-dimethylcyclohexane derivative(s) can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the 1-acetyl-3,3-dimethylcyclohexane derivative(s) employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the 1-acetyl-3,3-dimethylcyclohexane derivative(s) will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the 1-acetyl-3,3-dimethylcyclohexane derivative(s) ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein a 1-acetyl-3,3-dimethyl cyclohexane derivative is added to the foodstuff as an integral component of a flavoring composition, it is, of course, essential that the total quantity of flavoring composition employed be sufficient to yield an effective concentration in the foodstuff product.

Food flavoring compositions prepared in accordance with the present invention preferably contain the 1-acetyl-3,3-dimethylcyclohexane derivative(s) in concentrations from about 0.1 up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 1-acetyl-3,3-dimethylcyclohexane derivative(s) with, for example, gum arabic, gum tragacanth, carrageenan and the like, and thereafter spraydrying the resultant mixture whereby to obtain the particular solid product. Pre-prepared flavor mixes in powder form, e.g., a fruit-flavored powder mix are obtained by mixing the dried solid components, e.g., starch, sugar and the like and the 1-acetyl-3,3-dimethylcyclohexane derivative(s) in a dry blender until the requisite degree of uniformity is achieved.

It is presently preferred to combine with the 1-acetyl-3,3-dimethylcyclohexane derivative(s) of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methylfurfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal
2-Phenyl-2-hexenal;
2-Phenyl-2-pentenal;
3-Phenyl-4-pentenal diethyl acetal;
Damascone (1-crotonyl-2,2,6-trimethylcyclohex-1-one)
Damascenone (1-crotonyl-2,2,6-trimethylcyclohexa-1,5-diene)
Beta-cyclohomocitral (2,2,6-trimethyl-cyclohex-1-ene carboxaldehyde)
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxybenzene); and
2-(4-Hydroxy-4-methylpentyl)-norbornadiene prepared according to Example II of U.S. Pat. No. 3,911,028, issued on Oct. 7, 1975.

The 1-acetyl-3,3-dimethylcyclohexane derivative(s) of our invention and one or more auxiliary perfume ingredients, including, for example, alcohols, aldehydes, nitriles, esters, cyclic esters and natural essential oils, may be admixed so that the combined odors of the individual components produce a pleasant and desired fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the overall sensory effect of the perfume composition will be at least the sum total of the effects of each of the ingredients. Thus, one or more of the 1-acetyl-3,3-dimethylcyclohexane derivative(s) can be used to alter, modify or enhance the aroma characteristics of a perfume composition, for example, by utilizing or moderating the olfactory reaction contributed by another ingredient in the composition.

The amount of 1-acetyl-3,3-dimethylcyclohexane derivative(s) of our invention which will be effective in perfume compositions as well as in perfumed articles and colognes depends on many factors, including the other ingredients, their amounts and the effects which are desired. It has been found that perfume compositions containing as little as 0.01% of a 1-acetyl-3,3-dimethylcyclohexane derivative(s) or even less (e.g., 0.005%) can be used to impart a fruity, woody, piney aroma with armoise and floral nuances and slight chocolate undertones to soaps, cosmetics or other products. The amount employed can range up to 70% of the fragrance components and will depend on considerations of cost, nature of the end product, the effect desired on the finished product and the particular fragrance sought.

The 1-acetyl-3,3-dimethylcyclohexane derivative(s) of our invention is useful [taken alone or together with other ingredients in perfume compositions] as an olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of 1-acetyl-3,3-dimethylcyclohexane derivative(s) will suffice to impart an intense floral note to rose formulations. Generally, no more than 3% of 1-acetyl-3,3-dimethylcyclohexane based on the ultimate end product, is required in the perfume composition.

In addition, the perfume composition or fragrance composition of our invention can contain a vehicle, or carrier for the 1-acetyl-3,3-dimethylcyclohexane derivative(s). The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that the 1-acetyl-3,3-dimethylcyclohexane derivative(s) of our invention can be utilized to alter, modify or enhance sensory properties, particularly organoleptic properties, such as flavor(s) and/or fragrance(s) of a wide variety of consumable materials.

The following Examples serve to illustrate our invention and this invention is to be considered restricted thereto only as indicated in the appended claims.

All parts and percentages given herein are by weight unless otherwise specified.

EXAMPLE I

Preparation of 1-(3,3-Dimethylcyclohexyl)-4-Methyl-Cis and Trans-(2 and 3)-Penten-1-One Reaction:

A solution of 474 grams of 1-acetyl-3,3-dimethylcyclohexane, 500 ml methanol, 40 grams of NaOH and 50 ml toluene is heated to reflux. Isobutyraldehyde (240 grams), is added dropwise over a 45 minute period. The reaction mixture is heated to reflux for a further 90 minutes, at which time, the solution is cooled to room temperature and neutralized with hydrochloric acid. The methanol is removed by distillation, and the aqueous layer is removed from the resulting two phase mixture. The organic layer is washed once with water and distilled rapidly through a short column to afford a mixture of 1-(3,3-dimethylcyclohexyl)-4-methyl-cis and trans-(2 and 3)-penten-1-one (360 grams, 58%) [112°–117° C, 2.8 mm] and higher boiling products identified as:

Redistillation of this material through a 1½ × 12 inch Goodloe column gave the following fractions:

| Fraction No. | Vapor Temperature (° C) | Liquid Temperature (° C) | Vacuum mm Hg | Weight (g) | Reflux Ratio |
|---|---|---|---|---|---|
| 1 | 85–101 | 128 | 2.8 | 6.6 | 9:1 |
| 2 | 112 | 128 | 2.8 | 10.6 | 9:1 |
| 3 | 112 | 128 | 2.8 | 16.6 | 9:1 |
| 4 | 112 | 132 | 2.8 | 12.9 | 9:1 |
| 5 | 112 | 128 | 2.8 | 28.3 | 9:1 |
| 6 | 112 | 128 | 2.8 | 12.0 | 9:1 |
| 7 | 112 | 128 | 2.8 | 24.2 | 9:1 |
| 8 | 112 | 128 | 2.8 | 27.3 | 9:1 |
| 9 | 114 | 134 | 2.8 | 27.1 | 4:1 |
| 10 | 115 | 135 | 2.8 | 22.7 | 4:1 |
| 11 | 115 | 137 | 2.8 | 26.9 | 4:1 |
| 12 | 115 | 140 | 2.8 | 25.7 | 4:1 |
| 13 | 116 | 149 | 2.8 | 25.0 | 4:1 |
| 14 | 116 | 149 | 2.8 | 26.9 | 4:1 |
| 15 | 117 | 155 | 2.8 | 16.9 | 4:1 |
| 16 | 122 | 160 | 2.8 | 16.9 | 4:1 |
| 17 | 128 | 165 | 2.8 | 23.9 | 4:1 |
| 18 | 128 | 176 | 2.8 | 26.9 | 4:1 |
| 19 | 130 | 205 | 2.8 | 24.3 | 4:1 |
| 20 | 130 | 214 | 2.8 | 23.1 | 4:1 |
| 21 | 130 | 219 | 2.8 | 25.5 | 4:1 |
| 22 | 138 | 241 | 2.8 | 25.5 | 4:1 |
| 23 | 149 | 250 | 2.8 | 11.7 | 4:1 |

Fractions 5–13 contain greater than 99% desired product having the formulae:

The following fractions contain the following percentages of this mixture:

| Fraction No. | Percent Desired Product |
|---|---|
| 3 | 60 |
| 4 | 90 |
| 5–13 | >99 |
| 14 | 98 |

-continued

| Fraction No. | Percent Desired Product |
|---|---|
| 15 | 96 |
| 16 | 90 |
| 17 | 60 |
| 18 | 20 |

Fractions 5–13, from a fragrance standpoint, have fruity, woody, piney aromas with armoise, floral nuances and a slight chocolate undertone.

From a flavor standpoint, this material has a sweet, fruity, raspberry, woody, lemon, piney aroma with a sweet, raspberry and lemon flavor character.

EXAMPLE II

Preparation of 1-(3,3-Dimethylcyclohexyl)-4-Methyl-Cis and Trans-(2 and 3)-Penten-1-One Reaction:

A mixture of 1-acetyl-3,3-dimethylcyclohexane (462 grams), isobutyraldehyde (108 grams), boric acid (6.2 grams) and boron oxide (52 grams) is heated and stirred in an autoclave at 150° C for 5 hours. The solution is filtered from inorganic salts and washed three times with 10% HCl. Distillation affords 319 grams of 1-acetyl-3,3-dimethylcyclohexane and 138 grams of 1-(3,3-dimethylcyclohexyl)-4-methyl-cis and trans-(2 and 3)-penten-1-one (22%, based on charged 1-acetyl-3,3-dimethylcyclohexane.

Figure 1:
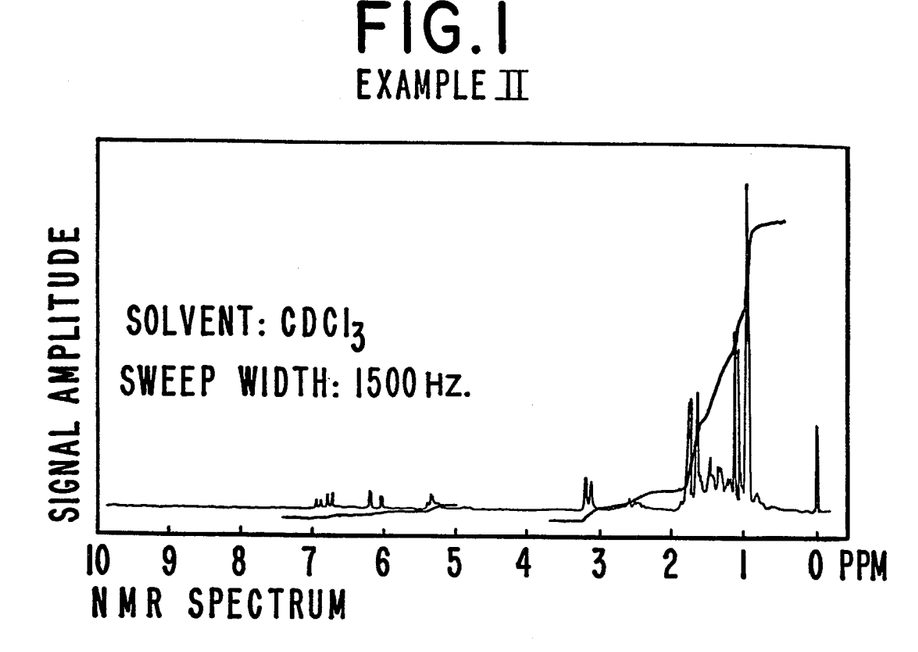
FIG. 1 represents the NMR spectrum for 1-(3,3-dimethylcyclohexyl)-4-methyl-cis and trans-(2 and 3)-penten-1-one produced according to Example II.
Figure 2:
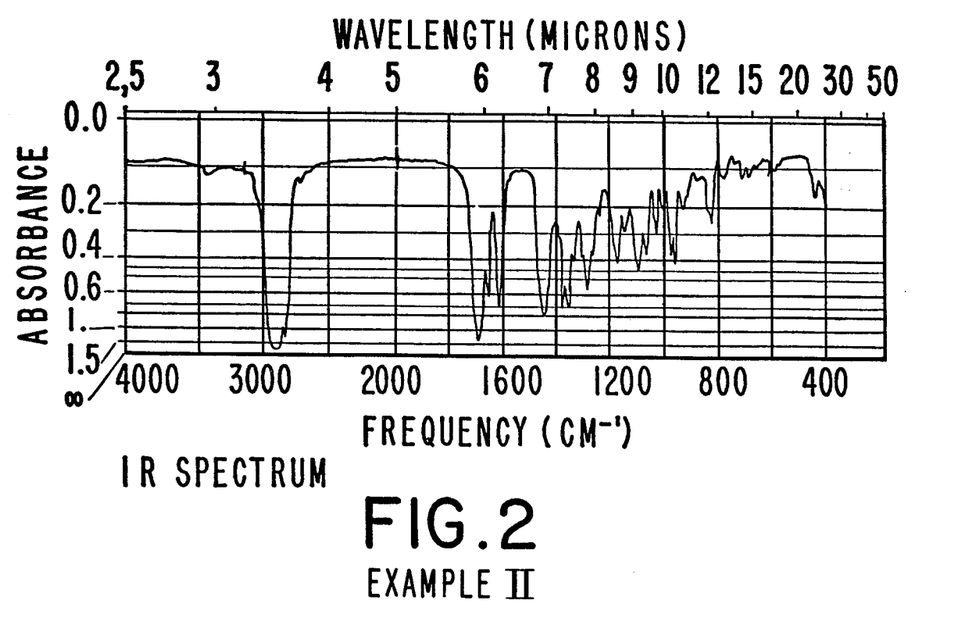
FIG. 2 represents the Infrared spectrum for 1-(3,3-dimethylcyclohexyl)-4-methyl-cis and trans-(2 and 3)-penten-1-one produced according to Example II.

The 1-(3,3-dimethylcyclohexyl)-4-methyl-cis and trans-(2 and 3)-penten-1-one is determined by NMR and Infrared analyses to be a mixture of:

and

The NMR spectrum for this mixture is set forth in FIG. 1. The Infrared spectrum for this mixture is set forth in FIG. 2.

The NMR analysis is as follows:

| ppm | Interpretation |
|---|---|
| 1.85 (s) | Methyl Groups "A" |
| 1.87 (s) | |
| 2.62 (d, J = 1 $H_z$) | Methyl Groups "C" |
| 2.76 (d, J = 1 $H_z$) | |
| 2.03 (s) | Methyl Groups "B" |
| 2.1 (s) | |
| 2.3–2.8 (broad multiplet) | $H_D$ |
| 3.14 (d, J = 7$H_z$) | $CH_2$ Group "E" |
| 5.28 (broad t, J = 7$H_z$) | $H_F$ |
| 6.0 and 6.28 (two multiplets) | $H_G$ |
| 6.68–6.92 (two multiplets) | $H_H$ |

The Infrared analysis is as follows:

| 1665 $cm^{-1}$ | |
| 1710 | |
| 1690 (sh) | C=O |
| 1720 (sh) | |
| 1620 $cm^{-1}$ | C=C |

EXAMPLE III

Synthesis of 1-(3,3-Dimethylcyclohexyl)-Cis and Trans-(2 and 3)-Penten-1-One

Reaction:

A mixture of 462 grams of 1-acetyl-3,3-dimethylcyclohexane, 87 grams of propionaldehyde, 52 grams boron oxide and 6.2 grams of boric acid is heated at 150°

C in an autoclave for 8 hours. After cooling to room temperature, the solution is filtered from inorganic salts, washed once with aqueous sodium carbonate and twice with saturated salt solution. Distillation through a short column afforded a mixture containing 367 grams of 1-acetyl-3,3-dimethylcyclohexane and 60 grams of 1-(3,3-dimethylcyclohexyl)-cis and trans-(2 and 3)-penten-1-one (20% based on charged propionaldehyde.

A portion of the distillate rich in the desired product(s) was distilled through a 1.5 × 12 inch Goodloe column giving the following fractions:

| Fraction No. | Vapor Temperature (° C) | Liquid Temperature (° C) | Vacuum mm Hg | Weight (g) | Reflux Ratio |
|---|---|---|---|---|---|
| 1 | 55–52 | 105–103 | 2.5 | 10.2 | 9:1 |
| 2 | 52 | 109 | 2.2 | 11.1 | 9:1 |
| 3 | 60 | 126 | 2.0 | 5.5 | 9:1 |
| 4 | 82 | 138 | 2.0 | 6.6 | 4:1 |
| 5 | 88 | 138 | 2.0 | 3.0 | 4:1 |
| 6 | 90 | 140 | 2.0 | 5.3 | 4:1 |
| 7 | 90 | 140 | 2.0 | 6.7 | 4:1 |
| 8 | 90 | 144 | 2.0 | 6.7 | 4:1 |
| 9 | 90 | 154 | 2.0 | 6.5 | 4:1 |
| 10 | 95 | 181 | 2.0 | 7.0 | 4:1 |
| 11 | 93 | 220 | 2.0 | 2.6 | 4:1 |

Figure 3:
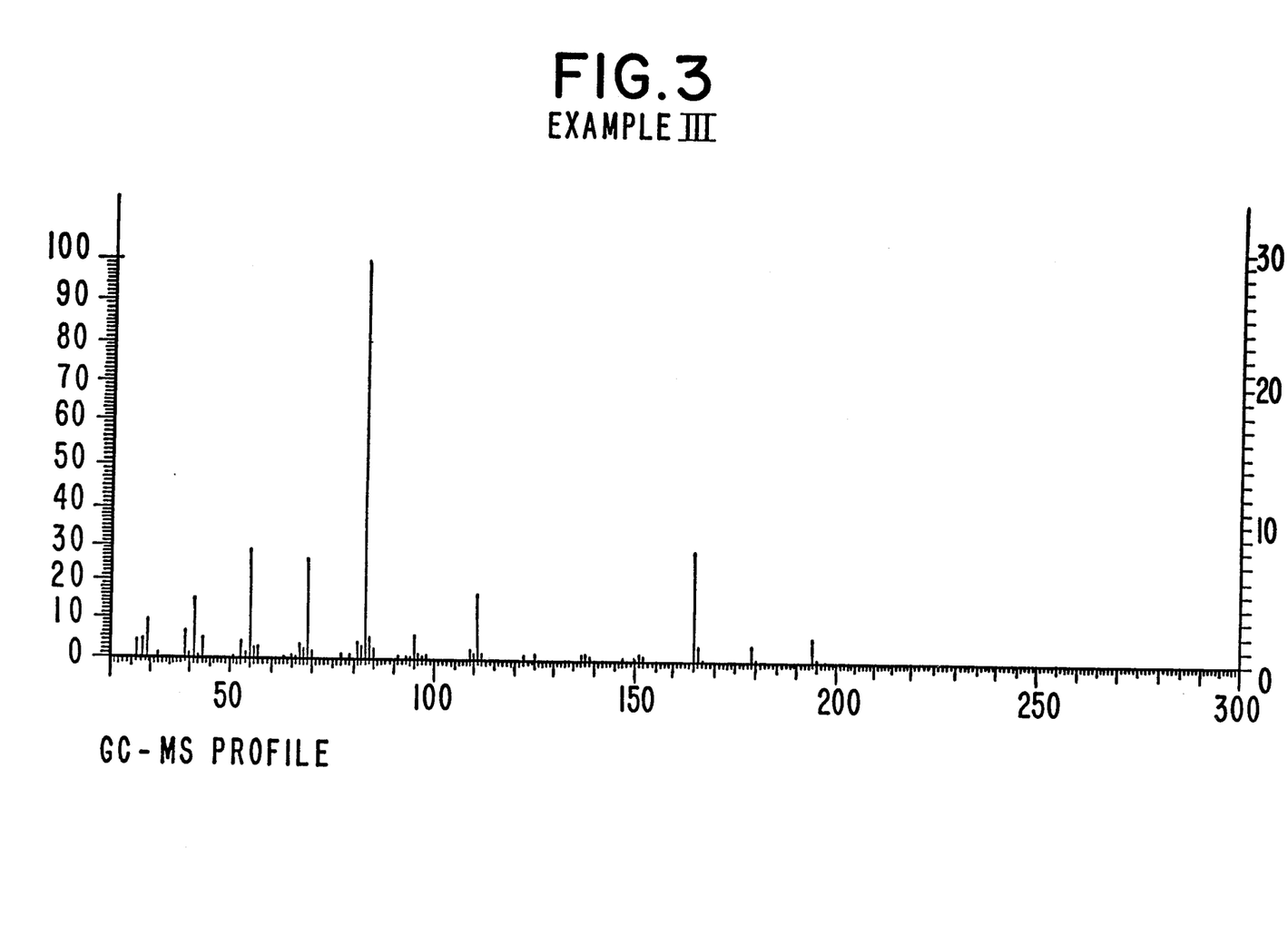
FIG. 3 represents the GC-MS profile for 1-(3,3-dimethylcyclohexyl)-cis and trans-(2 and 3)-penten-1-one produced according to Example III.
Figure 4:
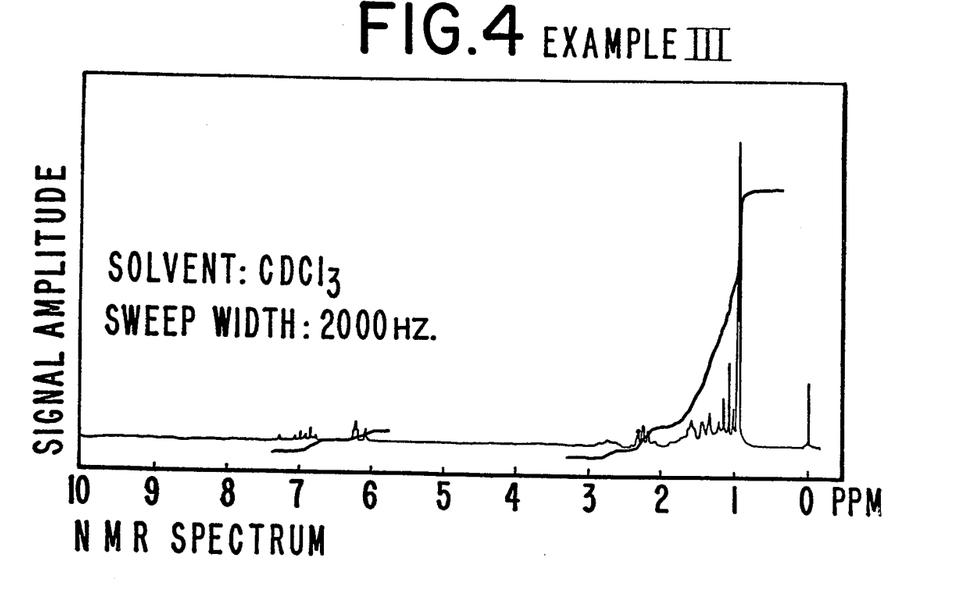
FIG. 4 represents the NMR spectrum for 1-(3,3-dimethylcyclohexyl)-cis and trans-(2 and 3)-penten-1-one produced according to Example III.
Figure 5:
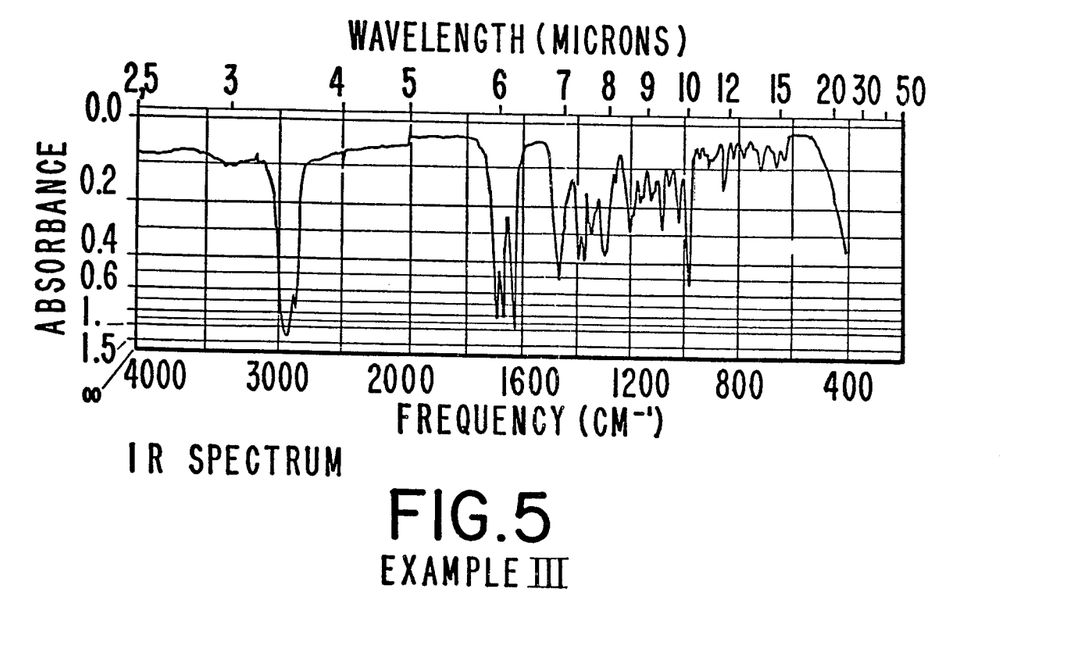
FIG. 5 represents the Infrared spectrum for 1-(3,3-dimethylcyclohexyl)-cis and trans-(2 and 3)-penten-1-one produced according to Example III.

Fraction #7, at 2 ppm, has a sweet, raspberry, fruity, piney, floral, ionone aroma and a sweet, sweet fruity, redberry, raspberry, piney, floral, ionone-like flavor. The mixture 1-(3,3-dimethylcyclohexyl)-cis and trans-(2 and 3)-penten-1-one is trapped out via preparative GLC and has the structure:

(cis and trans)

The GC-MS profile for this mixture is set forth in FIG. 3. The NMR spectrum is set forth in FIG. 4. The Infrared spectrum is set forth in FIG. 5.

The NMR analysis is as follows:

| δ, ppm | Interpretation |
|---|---|
| 1.95 (s, 6H) | $CH_3$ Groups "A" |
| 2.08 (t, 3, J=8$H_Z$) | $CH_3$ Groups "B" |
| 2.25 (quintet, 2H, J=8$H_Z$) | $CH_2$ Groups "C" |
| 2.7–2.9 (broad multiplet, 1H) | $H_D$ |
| 6.05 and 6.22 (two multiplets) | $H_E$ |
| 6.75–7.05 (m, 1H) | $H_F$ |

The Infrared analysis is as follows:
C=O 1665 and 1685 cm$^{-1}$
C=C 1620

EXAMPLE IV

Hydrogenation of 1-(3,3-Dimethylcyclohexyl)-4-Methyl-Cis and Trans-(2 and 3)-Penten-1-One Reaction:

Into a 250 cc Parr shaker is placed 107 grams of 1-(3,3-dimethylcyclohexyl)-4-methyl-cis and trans-(2 and 3)-penten-1-one prepared according to Example I, 1 gram of 5% Palladium-on-carbon catalyst and 125 grams of isopropyl alcohol. The Parr shaker is sealed and heated to a temperature of 125° C at a pressure of 50–150 psig of hydrogen and maintained at that pressure range and temperature range for a period of 1.5 hours. At the end of the 1.5 hour period, the reaction product is filtered and distilled in a 48 inch Vigreaux column. The distillation data is as follows:

| Fraction No. | Vapor Temperature (° C) | Liquid Temperature (° C) | Vacuum mm Hg | Weight (g) | Reflux Ratio |
|---|---|---|---|---|---|
| 1 | 67–89 | 118–126 | 2.2 | 3.8 | 9:1 |
| 2 | 91 | 137 | 2.2 | 3.7 | 9:1 |
| 3 | 91 | 129 | 2.2 | 7.4 | 4:1 |
| 4 | 91 | 129 | 2.2 | 8.6 | 4:1 |
| 5 | 91 | 129 | 2.2 | 13.4 | 4:1 |
| 6 | 91 | 129 | 2.2 | 14.0 | 4:1 |
| 7 | 91 | 131 | 2.2 | 15.2 | 4:1 |
| 8 | 91 | 156 | 2.2 | 14.7 | 4:1 |
| 9 | 94 | 187 | 2.2 | 8.2 | 4:1 |
| 10 | 98 | 240 | 2.2 | 3.5 | 4:1 |

From a food flavor standpoint, fraction #6, resulting from the distillation, has a sweet, piney, fruity, blueberry, woody aroma with a sweet, piney, fruity, nutmeat flavor character.

From a perfumery standpoint, bulked fractions #2–9, at 10% in food grade alcohol, have a low-keyed, sweet woody aroma with chocolate-like nuances.

Figure 6:
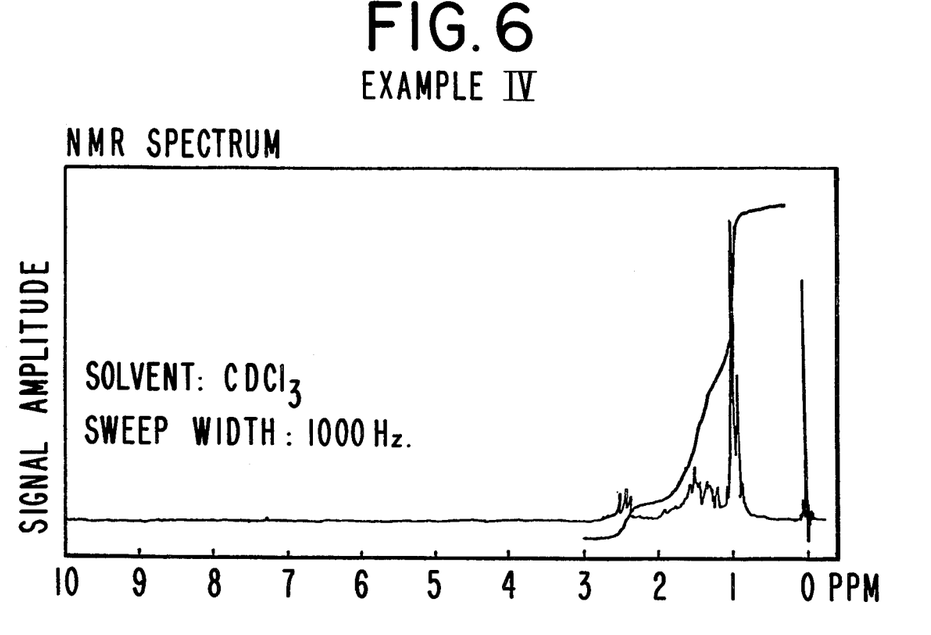
FIG. 6 represents the NMR spectrum for 3,3-dimethyl-1-(4-methylvaleryl)-cyclohexane produced according to Example IV.
Figure 7:
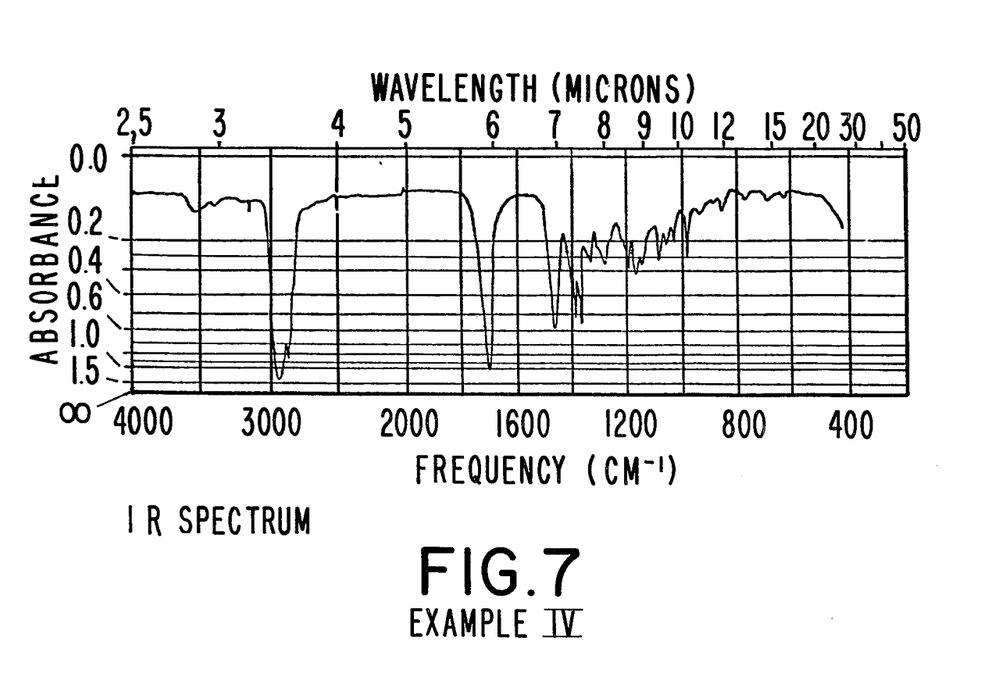
FIG. 7 represents the Infrared spectrum for 3,3-dimethyl-1-(4-methylvaleryl)-cyclohexane produced according to Example IV.

Fraction #7 is determined by NMR, Infrared and Mass Spectral analyses to have the structure:

The NMR analysis is as follows:

| δ ppm | Interpretation |
|---|---|
| 0.82–0.98 (m, 12H) | $CH_3$ Groups |
| 2.43 (t, 2H, J=8$H_Z$) | Methylene "A" |

The Infrared analysis is as follows:
2950 cm$^{-1}$
2870
1700
1560 (C=O)
1390
1360

The Mass Spectral analysis is as follows: 111, 41, 43, 69, 55 and 27

The NMR spectrum for this compound is set forth in FIG. 6. The Infrared spectrum for this compound is set forth in FIG. 7.

EXAMPLE V

Raspberry Flavor Formulation

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

1-(3,3-Dimethylcyclohexyl)-4-methyl-cis and trans-(2 and 3)-penten-1-one prepared according to Example I is added to half of the above formulation at the rate of 2.0%. The formulation with the 1-(3,3-dimethylcyclohexyl)-4-methyl-cis and trans-(2 and 3)-penten-1-one is compared with the formulation without the 1-(3,3-dimethylcyclohexyl)-4-methyl-cis and trans-(2 and 3)-penten-1-one at the rate of 0.01 percent (100 ppm) in water and evaluated by a bench panel.

The flavor containing the 1-(3,3-dimethylcyclohexyl)-4-methyl-cis and trans-(2 and 3)-penten-1-one is found to have substantially sweeter aroma notes and a sweet raspberry, raspberry kernel-like and sweet aftertaste and mouthfeel missing in the basic raspberry formulation. It is the unanimous opinion of the bench panel that the chemical, 1-(3,3-dimethylcyclohexyl)-4-methyl-cis and trans-(2 and 3)-penten-1-one rounds the flavor out and contributes to a very natural fresh aroma and taste as found in full ripe raspberries. Accordingly, the flavor with the addition of the 1-(3,3-dimethylcyclohexyl)-4-methyl-cis and trans-(2 and 3)-penten-1-one is considered as substantially better than the flavor without 1-(3,3-dimethylcyclohexyl)-4-methyl-cis and trans-(2 and 3)-penten-1-one.

EXAMPLE VI

Raspberry Flavor Formulation

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

1-(3,3-Dimethylcyclohexyl)-cis and trans-(2 and 3)-penten-1-one prepared according to Example III is added to half of the above formulation at the rate of 2.0%. The formulation with the 1-(3,3-dimethylcyclohexyl)-cis and trans-(2 and 3)-penten-1-one is compared with the formulation without the 1-(3,3-dimethylcyclohexyl)-cis and trans-(2 and 3)-penten-1-one at the rate of 0.01 percent (100 ppm) in water and evaluated by a bench panel.

The flavor containing the 1-(3,3-dimethylcyclohexyl)-cis and trans-(2 and 3)-penten-1-one is found to have substantially sweeter aroma notes and a sweet raspberry, raspberry kernel-like and sweet aftertaste and mouthfeel missing in the basic raspberry formulation. It is the unanimous opinion of the bench panel that the chemical, 1-(3,3-dimethylcyclohexyl)-cis and trans-(2 and 3)-penten-1-one rounds the flavor out and contributes to a very natural fresh aroma and taste as found in full ripe raspberries. Accordingly, the flavor with the addition of the 1-(3,3-dimethylcyclohexyl)-cis and trans-(2 and 3)-penten-1-one is considered as substantially better than the flavor without 1-(3,3-dimethylcyclohexyl)-cis and trans-(2 and 3)-penten-1-one.

EXAMPLE VII

A. Powder Flavor Composition

20 Grams of the flavor composition of Example V is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel speed of 50,000 r.p.m.

B. Sustained Release Flavor

The following mixture is prepared:

| Ingredient | Parts by Weight |
|---|---|
| Liquid Raspberry Flavor Composition of Example V | 20 |
| Propylene glycol | 9 |
| Cab-O-Sil ®M-5 (Brand of Silica produced by the Cabot Corporation of 15 High Street, Boston, Mass. 02110; Physical Properties: Surface Area: 200 m²/gm Nominal particle size: 0.012 microns Density: 2.3 lbs/cu.ft.) | 5.00 |

The Cab-O-Sil is dispersed in the liquid raspberry flavor composition of Example V with vigorous stirring, thereby resulting in a viscous liquid. 71 Parts by weight of the powder flavor composition of Part A, supra, is then blended into the said viscous liquid, with stirring at 25° C for a period of 30 minutes resulting in a dry, free flowing sustained release flavor powder.

EXAMPLE VIII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example VI is added to the solution which is then homogenized to form an emulsion having particle size typically in the range of 2-5 microns. This material is kept at 120° F. under which conditions the gelatin will not jell.

Coascervation is induced by adding, slowly and uniformly 40 parts by weight of a 20% aqueous solution of sodium sulphate. During coascervation, the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE IX

Chewing Gum

100 Parts by weight of chicle are mixed with 4 parts by weight of the flavor prepared in accordance with Example VII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE X

Chewing Gum

100 Parts by weight of chicle are mixed with 18 parts by weight of the flavor prepared in accordance with Example VIII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE XI

Toothpaste Formulation

The following separate groups of ingredients are prepared:

| Parts by Weight | Ingredient |
|---|---|
| Group "A" | |
| 30.200 | Glycerin |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalcium phosphate (Dihydrate) |
| Group "C" | |
| 2.000 | Sodium N-Lauroyl Sarcosinate (foaming agent) |
| Group "D" | |
| 1.200 | Flavor Material of Example VII |
| 100.00 (Total) | |

PROCEDURE

1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant raspberry flavor, of constant strong intensity throughout said procedure (1–1.5 minutes).

EXAMPLE XII

Chewable Vitamin Tablets

The flavor material produced according to the process of Example VIII is added to a Chewable Vitamin Tablet Formulation at a rate of 10 gm/Kg which Chewable Vitamin Tablet Formulation is prepared as follows:

In a Hobart Mixer, the following materials are blended to homogeneity:

| | Gms/1000 tablets |
|---|---|
| Vitamin C (ascorbic acid) as ascorbic acid-sodium ascorbate mixture 1:1 | 70.0 |
| Vitamin $B_1$ (thiamine mononitrate) as Rocoat ® thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example XXVIII | (as indicated above) |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.66 g Vitamin D are then added as beadlets. The entire blend is then compressed using concave punches at 0.5 g each.

Chewing of the resultant tablets yields a pleasant, long-lasting, consistently strong raspberry flavor for a period of 12 minutes.

EXAMPLE XIII

Blueberry Fondant Formulation

The following blueberry fondant formulation is prepared:

| Ingredient | Parts by Weight |
|---|---|
| Oil of Cardamom | 0.25 |
| Oil of Cloves | 0.50 |
| Oil of Galanga | 1.00 |
| Oil of Cinnamon | 1.25 |
| Oil of Coriander | 2.50 |
| Oil of Fennel | 2.50 |
| Amyl Acetate | 22.00 |
| Benzyl Benzoate | 33.00 |
| 1-(3,3-dimethylcyclohexyl)-4-methyl-cis and trans-(2 and 3)- | 37.00 |

| Ingredient | Parts by Weight |
|---|---|
| penten-1-one, fraction #6 produced according to Example IV | 0.1 |

The 1-(3,3-dimethylcyclohexyl)-4-methyl-cis and trans-(2 and 3)-penten-1-one produced according to Example V adds sweet, piney, fruity and woody nuances to the blueberry fondant formulation thereby causing it to be more natural-like in taste and aroma.

EXAMPLE XIV

A perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petigrain SA | 20 |
| Bergamot Oil | 30 |
| Alpha Methyl Ionone | 25 |
| 1-(3,3-dimethylcyclohexyl)-4-methyl-cis and trans-(2 and 3)-penten-1-one produced according to Example II | 10 |
| Cyclized Bicyclo C-12 material produced according to the process of Example IV of Canadian Patent 854,225, issued on October 20, 1970 | 5 |
| Isobornyl cyclohexyl alcohol | 10 |
| Benzyl Acetate | 25 |
| 2-n-Heptylcyclopentanone | 5 |
| | 353.3  (TOTAL) |

The foregoing blend is evaluated and found to have a high degree of richness and persistence in its novel natural amber qaulity. This base composition can be admixed with aqueous ethanol, chilled and filtered to produce a finished cologne. The cologne so prepared has an amber aroma leaning towards a woody amber note with an excellent armoise nuance. The base composition can also be used to scent soap or other toilet goods such as lotion, aerosol, sprays and the like.

EXAMPLE XV

Preparation Of A Cosmetic-Powder Composition

A cosmetic powder is prepared by mixing in a ball mill, 100 g of talcum powder with 0.25 g of 1-(3,3-dimethylcyclohexyl)-4methyl-cis and trans-(2 and 3)-penten-1-one prepared according to Example II. It has an excellent piney, woody, floral and fruity aroma.

EXAMPLE XVI

Perfumed Liquid Detergent

Concentrated liquid detergents (Lysine salt of n-dodecylbenzene sulfonic acid as more specifically described in U.S. Pat. No. 3,948,818, issued on Apr. 6, 1976) with a piney, woody odor are prepared containing 0.10, 0.15 and 0.20% of 1-(3,3-dimethylcyclohexyl)-4-methyl-cis and trns-(2 and 3)-penten-1-one prepared according to Example II. They are prepared by adding and homogeneously mixing the appropriate quantity of 1-(3,3-dimethylcyclohexyl)-4-methyl-cis and trans-(2 and3)-penten-1-one in the liquid detergent. The detergents all possess a piney, woody fragrance, the intensity increasing with greater concentrations of 1-(3,3-dimethylcyclohexyl)-4-methyl-cis and trans-(2 and 3)-penten-1-one.

EXAMPLE XVII

Preparation of a Cologne and Handkerchief Perfume 1-(3,3-Dimethylcyclohexyl)-4-methyl-cis and trans-(2 and 3)-penten-1-one prepared according to the process of Example II is incorporated in a cologne at a concentration of 2.5% in 85% aqueous ethanol; and into a handkerchief perfume at a concentration of 20% (in 95% aqueous ethanol). A distinct and definite piney, woody fragrance is imparted to the cologne and to the handkerchief perfume.

EXAMPLE XVIII

Preparation of a Cologne and Handkerchief Perfume

The composition of Example XIV is incorporated in a cologne at a concentration of 2.5% in 85% aqueous ethanol; and into a handkerchief perfume at a concentration of 20% (in 95% aqueous ethanol). The use of 1-(3,3-dimethylcyclohexyl)-4-methyl-cis and trans-(2 and 3)-penten-1-one in the composition of Example II affords a distinct and definite strong amber aroma with piney, woody notes to the handkerchief perfume and cologne.

EXAMPLE XIX

Preparation of Soap Composition

One hundred grams of soap chips are mixed with one gram of 1-(3,3-dimethylcyclohexyl)-4-methyl-cis and trans-(2 and 3)-penten-1-one of Example II until a substantially homogeneous composition is obtained. The perfumed soap composition manifests an excellent woody, piney aroma.

EXAMPLE XX

Preparation of a Detergent Composition

A total of 100 g of a detergent powder (Lysine salt of n-dodecyl benzene sulfonic acid as more specifically described in U.S. Pat. No. 3,948,818, issued on Apr. 6, 1976) is mixed with 0.15 g of the 1-(3,3-dimethylcyclohexyl)-4-methyl-cis and trans-(2 and 3)-penten-1-one of Example II until a substantially homogeneous composition is obtained. This composition has an excellent woody, piney aroma.

What is claimed is:

1. A process for augmenting or enhancing the aroma or taste of a foodstuff which comprises adding thereto from 0.5 parts per million up to about 100 parts per million based on the total composition of a compound having the structure:

2. A flavor augmenting or enhancing composition comprising (i) from about 0.1 up to about 15% by weight based on the total weight of said flavoring composition of a compound having the structure:

and (ii) the remainder of said composition being one or more flavor adjuvants selected from the group consisting of p-hydroxybenzyl acetone, maltol, benzyl acetate, methyl cinnamate, geraniol, ethyl methyl phenyl glycidate, vanillin, methyl anthranilate, alpha-ionone, gamma undecalactone, ethyl pelargonate, isoamyl acetate, acetaldehyde, dimethyl sulfide, isobutyl acetate, acetic acid, ethyl butyrate, diacetyl, anethole, cis-3-hexenol-1, naphthyl ethyl ether, ethyl acetate, isoamyl butyrate, 2-methyl-2-pentenoic acid, 2-(4-hydroxy-4-methyl-pentyl)norbornadiene, 4-allyl-1,2,6-trimethoxybenzene, cassia oil, eugenol, caryophyllene, guiacol, cinnamaldehyde, 5-methylfurfural, cuminaldehyde, cinnamyl formate, methyl cinnamate, furfural, 2,3-dimethylpyrazine, 2-ethyl-3-methylpyrazine, 3-phenyl-4-pentenal, 2-phenyl-2-hexenal, 2-phenyl-2-pentenal, 3-phenyl-4-pentenal diethyl acetal, 1-crotonyl-2,2,6-trimethylcyclohex-1-ene, 1-crotonyl-2,2,6-trimethylcyclohexa-1,5-diene, 2,2,6-trimethyl-cyclohex-1-ene carboxaldehyde and 4-propenyl-1,2,6-trimethoxybenzene.

* * * * *